US008241265B2

(12) United States Patent
Moy et al.

(10) Patent No.: US 8,241,265 B2
(45) Date of Patent: Aug. 14, 2012

(54) MEDICAMENT ADMIXING SYSTEM

(75) Inventors: Yei F. Moy, Buffalo Grove, IL (US);
Stanley F. Pytel, Third Lake, IL (US);
John S. Ziegler, Arlington Heights, IL
(US); Jesse C. Darley, Madison, WI
(US); Douglas S. Rodenkirch, Arlington
Heights, IL (US)

(73) Assignee: Hospira, Inc., Lake Forest, IL (US)

( * ) Notice: Subject to any disclaimer, the term of this patent is extended or adjusted under 35 U.S.C. 154(b) by 481 days.

(21) Appl. No.: 12/184,005

(22) Filed: Jul. 31, 2008

(65) Prior Publication Data
US 2009/0036866 A1 Feb. 5, 2009

Related U.S. Application Data

(60) Provisional application No. 60/953,287, filed on Aug. 1, 2007.

(51) Int. Cl.
*A61M 5/32* (2006.01)
*A61B 19/00* (2006.01)
(52) U.S. Cl. ........................... 604/416; 604/410
(58) Field of Classification Search .......... 604/403–416, 604/82, 86–88
See application file for complete search history.

(56) References Cited

U.S. PATENT DOCUMENTS

| | | | |
|---|---|---|---|
| 2,176,923 A | 10/1939 | Nitardy | |
| 2,372,181 A | 3/1945 | Barr | |
| 3,290,017 A | 12/1966 | Davies et al. | |
| 3,464,414 A | 9/1969 | Sponnoble | |
| 3,532,254 A | 10/1970 | Burke et al. | |
| 3,872,992 A | 3/1975 | Larson | |
| 4,089,432 A | 5/1978 | Crankshaw et al. | |
| 4,102,451 A | 7/1978 | Clarke et al. | |
| 4,185,747 A | 1/1980 | Goncalves | |
| 4,194,640 A | 3/1980 | Crankshaw et al. | |
| 4,226,334 A | 10/1980 | Weiler et al. | |

(Continued)

FOREIGN PATENT DOCUMENTS
DE 297 21 872 3/1998
(Continued)

OTHER PUBLICATIONS

European Search Report issued by the European Patent Office in Application No. 10160160.7 dated Oct. 6, 2010 (providing a concise summary of DE 297 21 872).

*Primary Examiner* — Tatyana Zalukaeva
*Assistant Examiner* — Philip R Wiest
(74) *Attorney, Agent, or Firm* — Brian R. Woodworth

(57) ABSTRACT

A system for mixing or reconstituting a drug contained in a first container with a diluent or fluid contained in a second container. The second container has a port docking assembly for engaging the first container. The first container is rotatable and axially slidable within the port docking assembly. The port docking assembly has an actuator to urge a stopper fluidly sealing the first container into the interior of the first container. The port docking assembly further includes a movable plug constructed to fluidly seal the second container in a first, docked position and to provide access to the interior of the second container in a second, activated position, whereby fluid communication between the first and second containers is provided when the first and second containers are in the second, activated position.

19 Claims, 8 Drawing Sheets

U.S. PATENT DOCUMENTS

| | | |
|---|---|---|
| 4,394,922 A | 7/1983 | Wimmer |
| 4,458,811 A | 7/1984 | Wilkinson |
| 4,610,684 A | 9/1986 | Knox et al. |
| 4,614,267 A | 9/1986 | Larkin |
| 4,614,515 A * | 9/1986 | Tripp et al. .................. 604/403 |
| 4,703,864 A | 11/1987 | Larkin et al. |
| 4,757,911 A | 7/1988 | Larkin et al. |
| 4,784,259 A | 11/1988 | Grabenkort |
| 4,784,658 A | 11/1988 | Grabenkort |
| 4,871,354 A | 10/1989 | Conn et al. |
| 4,936,841 A | 6/1990 | Aoki et al. |
| 4,948,000 A | 8/1990 | Grabenkort |
| 4,963,441 A | 10/1990 | Takai et al. |
| 4,998,671 A | 3/1991 | Lefheit |
| 5,064,059 A | 11/1991 | Ziegler et al. |
| 5,088,994 A | 2/1992 | Porat et al. |
| 5,102,408 A | 4/1992 | Hanacher |
| 5,176,526 A | 1/1993 | Hillbish et al. |
| 5,335,773 A | 8/1994 | Haber et al. |
| 5,358,501 A | 10/1994 | Meyer |
| 5,380,315 A | 1/1995 | Isono et al. |
| 5,423,793 A | 6/1995 | Isono et al. |
| 5,462,526 A | 10/1995 | Barney et al. |
| 5,526,853 A | 6/1996 | McPhee et al. |
| 5,785,701 A | 7/1998 | Sams et al. |
| 5,928,213 A | 7/1999 | Barney et al. |
| 5,944,709 A | 8/1999 | Barney et al. |
| 6,071,270 A * | 6/2000 | Fowles et al. .................. 604/413 |
| 6,203,535 B1 | 3/2001 | Barney et al. |
| 6,258,078 B1 | 7/2001 | Thilly |
| 6,846,305 B2 | 1/2005 | Smith et al. |
| 6,910,573 B2 | 6/2005 | Deans |
| 7,473,246 B2 | 1/2009 | Vancaillie et al. |
| 7,540,863 B2 | 6/2009 | Haindl |
| 7,615,041 B2 | 11/2009 | Sullivan et al. |
| 2004/0186457 A1 | 9/2004 | Truitt et al. |
| 2005/0045669 A1 | 3/2005 | Thunberg et al. |
| 2006/0282061 A1 | 12/2006 | Domkowski et al. |
| 2007/0088315 A1 | 4/2007 | Haindl |
| 2007/0102393 A1 | 5/2007 | Colin et al. |
| 2009/0032489 A1 | 2/2009 | Moy et al. |
| 2009/0036861 A1 | 2/2009 | Moy et al. |
| 2009/0036864 A1 | 2/2009 | Moy et al. |
| 2009/0036865 A1 | 2/2009 | Moy et al. |

FOREIGN PATENT DOCUMENTS

| | | |
|---|---|---|
| EP | 0 335 378 | 10/1989 |
| EP | 0 503 867 | 2/1997 |
| WO | 9814163 | 4/1998 |

* cited by examiner

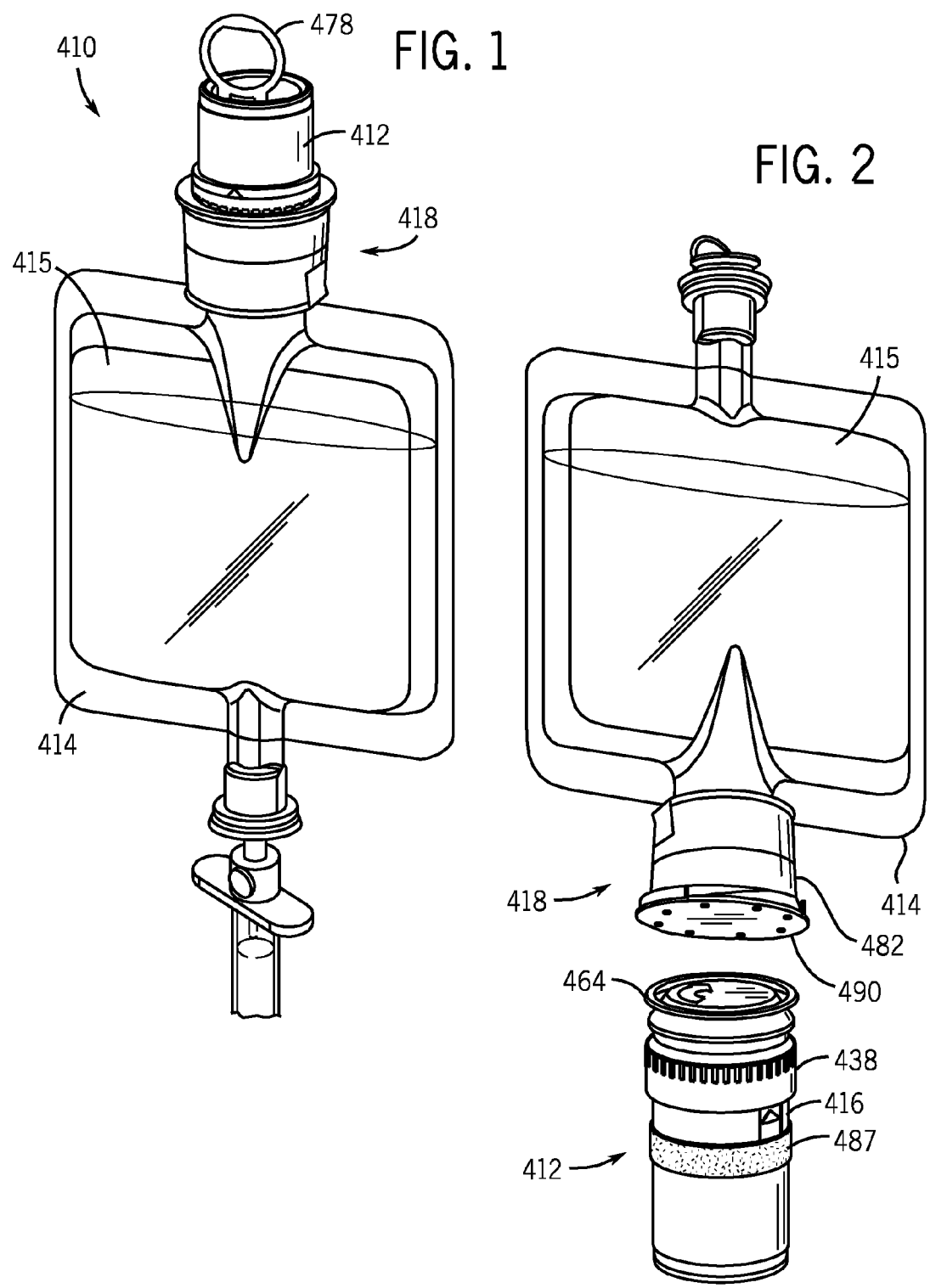

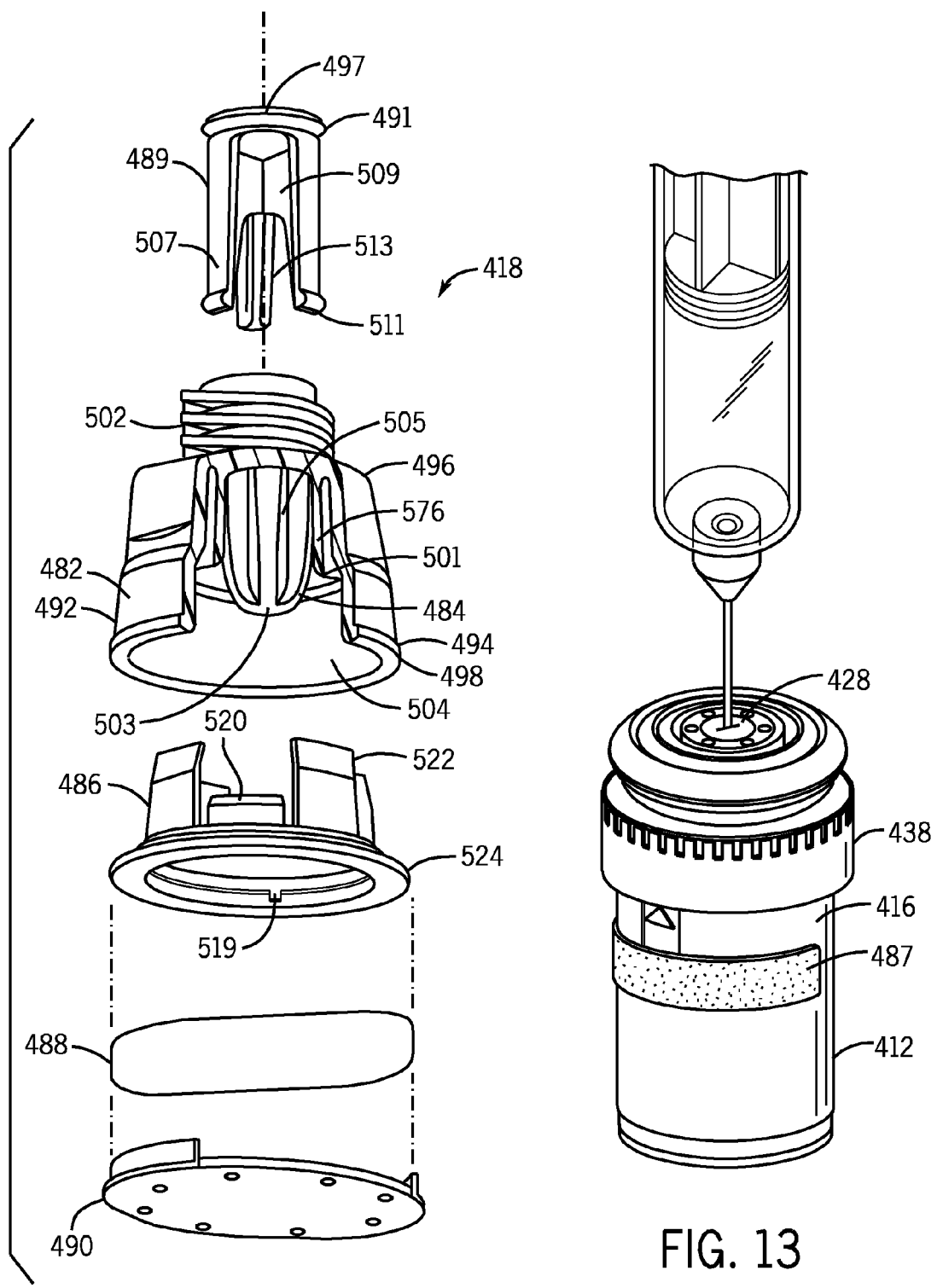

MEDICAMENT ADMIXING SYSTEM

TECHNICAL FIELD

The invention relates generally to a system and method for mixing the contents of two containers, and more particularly to a system for mixing or reconstituting a medicament contained in a first container with a diluent contained in a second container.

BACKGROUND OF THE INVENTION

Medicaments or drugs administered in a health care environment are typically packaged in vials whose interior is maintained in a sterile condition. The vials themselves are sealed by a sterile stopper which is typically pierced by a cannula when it is desired to remove the medicament or drug. Several procedures are required to get the drug from the vial into the body of a patient. Each procedure potentially jeopardizes the sterility of the vial, the stopper or the medicament. Further, if the medicament in a particular vial is a powder or is concentrated, there is often a need to add diluent to the vial to dissolve the powder or to dilute the concentrated medicament solution to the desired strength. Devices providing separate compartments in a single container for separately enclosing different components in such as way that they may be later intermixed are described in various U.S. patents, including U.S. Pat. No. 2,176,923 to Nitardy; U.S. Pat. No. 3,290,017 to Davies et al.; and, U.S. Pat. No. 3,532,254 to Burke et al. Additional devices of this type are disclosed in other U.S. patents, including U.S. Pat. No. 4,458,811 to Wilkinson; U.S. Pat. No. 4,610,684 to Knox, et al.; U.S. Pat. No. 4,998,671 to Lefheit; U.S. Pat. No. 5,102,408 to Hanacher; U.S. Pat. No. 5,176,526 to Barney, et al.; U.S. Pat. No. 5,462,526 to Barney, et al.; U.S. Pat. No. 5,928,213 to Barney, et al.; U.S. Pat. No. 5,944,709 to Barney, et al.; U.S. Pat. No. 6,203,535 to Barney, et al.; and U.S. Pat. No. 6,846,305 to Smith, et al.

Additionally, dual compartmented container systems having the means to intermix the contents of the two containers are also known in the art. For example, Hospira, Inc., the assignee of the present invention, owns numerous patents relating to such technology, including U.S. Pat. Nos. 4,614,267; 4,614,515; 4,757,911; 4,703,864; 4,784,658; 4,784,259; 4,948,000; 4,963,441; and, 5,064,059. Such delivery systems are manufactured and sold by Hospira, Inc. under the ADD-VANTAGE® trademark.

Accordingly, reconstitution systems and systems to intermix the contents of two containers from outside the container are well known in the art. While such reconstitution systems according to the prior art provide a number of advantageous features, they nevertheless have certain limitations. The present invention seeks to overcome certain of these limitations and other drawbacks of the prior art, and to provide new features not heretofore available. A full discussion of the features and advantages of the present invention is deferred to the following detailed description, which proceeds with reference to the accompanying drawings.

SUMMARY OF THE INVENTION

The present invention generally provides a system for mixing or reconstituting a drug contained in a first container with a diluent contained in a second container. In one embodiment the first container has a body cap that engages a port assembly connected to the second container to provide for fluid communication between a cavity of the first container and a cavity of the second container.

According to one embodiment, the first container is a drug container. The drug container has a neck and an opening in the neck leading to a cavity. A stopper is positioned within the opening of the first container to close off access to the cavity of the first container. The body cap is positioned around the neck and body portions of the container body. The body cap has a first mating member adapted to be received by a second mating member of the second container for connecting the first container to the second container. In one embodiment the first mating member comprises a flange extending from the body cap.

According to another embodiment, the second container is a diluent container, such as an IV bag. The diluent container has a port assembly extending therefrom. The port assembly is designed to receive the first container to place the contents of the first container in fluid communication with the contents of the second container.

According to another embodiment, the port assembly has a first opening at a proximal end thereof providing access to a cavity of the port housing, a second opening opposing the first opening, and a moveable plug sealing the second opening. According to another embodiment, the port housing has a second mating member adapted to engage the first mating member of the first container for connecting the second container to the first container. In one embodiment the second mating member is a retainer having a plurality of different length tabs to engage the first container in different axial positions.

According to another embodiment, the first set of tabs are utilized to assist in docking the first container in the port housing, and preferably preventing the first container from being removed from the port housing following docking, i.e., in a docked, non-activated position. In another embodiment, the second set of tabs is utilized to assist in maintaining the first container in an activated position.

According to another embodiment, the stopper transitions from a first position within the opening of the neck of the container body, to a second position within the cavity of the container body. When the stopper is in the second position medicament can flow through the opening in the first container According to another embodiment, the port assembly has an integral actuator. The actuator is positioned within the cavity of the port housing. In one embodiment, the actuator has a proximal end, a distal end, and a central cavity. In another embodiment the actuator is comprised of a plurality of axial sidewall members with axial gaps between the sidewall members.

According to another embodiment, a system for mixing a medicament in a first container with a sterile fluid in a second container is provided. The system comprises an activation collar connected to the first container.

According to another embodiment, the first container has a recessed track on an outer surface thereof, and the activation collar has a protrusion that mates with the track. The geometry of the track dictates allowable movement of the first container.

According to another embodiment, a visual indicator is provided on the outer surface of the first container. The visual indicator is generally visible when the first container is in the first or docked position. However, the visual indicator is generally hidden within the port assembly when the first container is in the second or activated position, thereby providing a positive visual indication of activation.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 1 is a perspective view of one embodiment of the presents invention in which a first container is docked to a second container and activated to allow for reconstitution of a drug in the first container with a diluent in the second container, with the system shown in the hanging position for use;

FIG. 2 is a perspective view of one embodiment of a first container in accordance with the present invention and a second container in accordance with the present invention, the second container having a docking port, the first and second containers being depicted prior to docking and activation of the first container to the second container;

FIG. 3 is a perspective exploded view of one embodiment of the docking assembly for the second container in accordance with the present invention;

DETAILED DESCRIPTION

Figure 4:
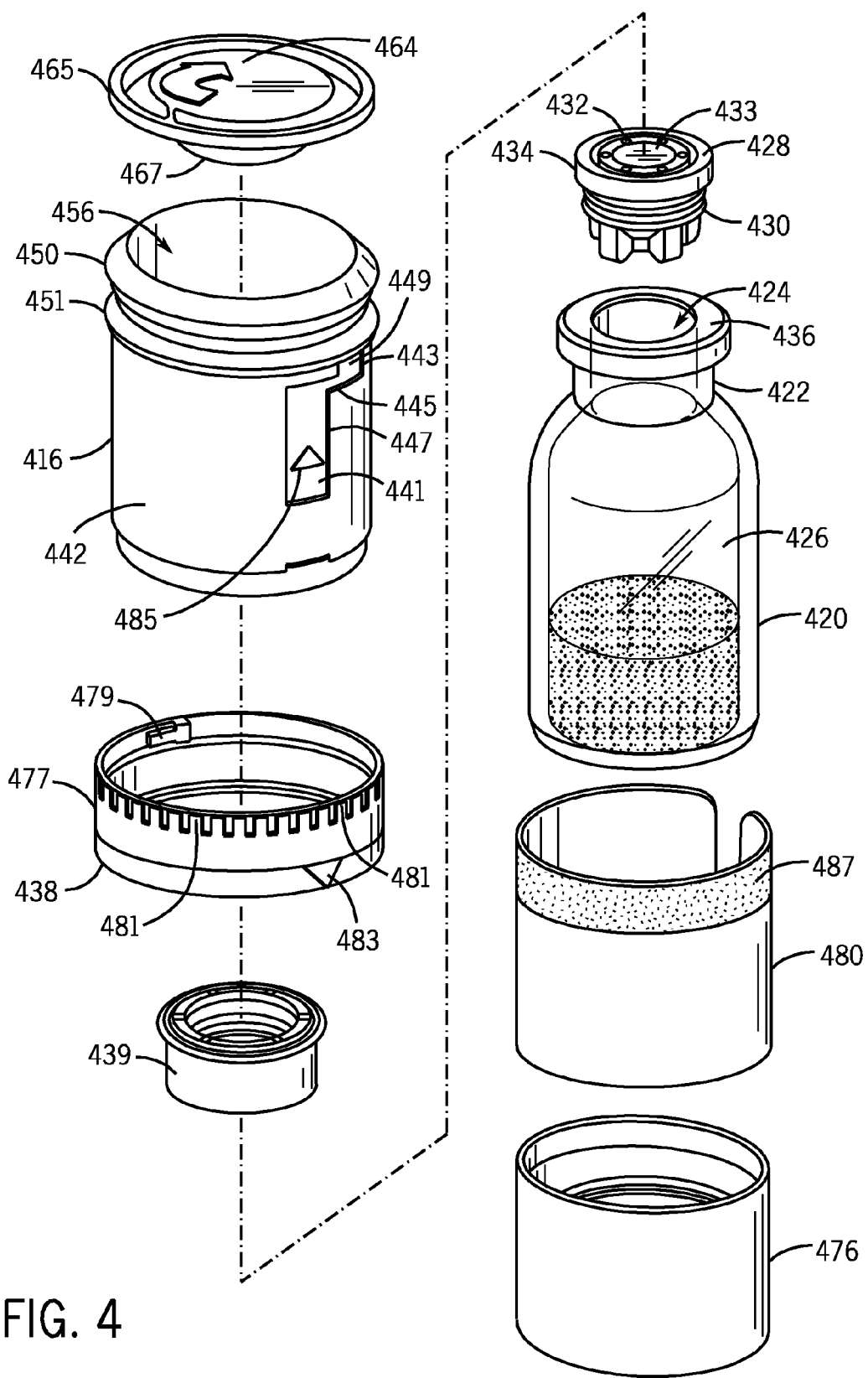
FIG. 4 is an exploded perspective view of one embodiment of the first container depicted in FIG. 1.
Figure 5:
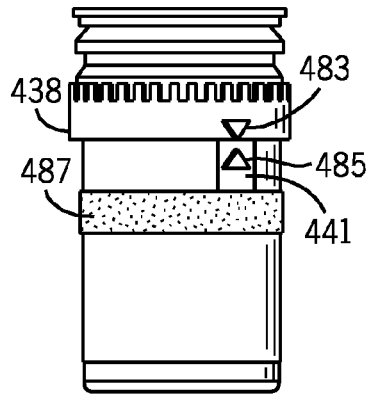
FIG. 5 is a front elevation view of the first container shown in a simulated docked position.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring now to the Figures, and specifically to FIGS. 1 and 2, there is shown a two-part admixing or reconstitution system 410 comprised of a first container 412 and a second container 414. In one embodiment, the first container 412 is a medicament or drug container 412 and is preferably in the form of a vial with an exterior housing, and the second container 414 is a diluent container and is preferably in the form of a flexible bag. In a one embodiment the diluent container 414 is a flexible container formed from first and second opposing sheets of flexible material that are joined and sealed at the edges to provide a fluid tight cavity for containing a diluent therein. At one edge thereof, the opposing sheets of the flexible diluent container 414 are sealed around the port housing 482 of the port assembly 418 to fixedly connect the port assembly 418 to the second container 414.

Figure 10:
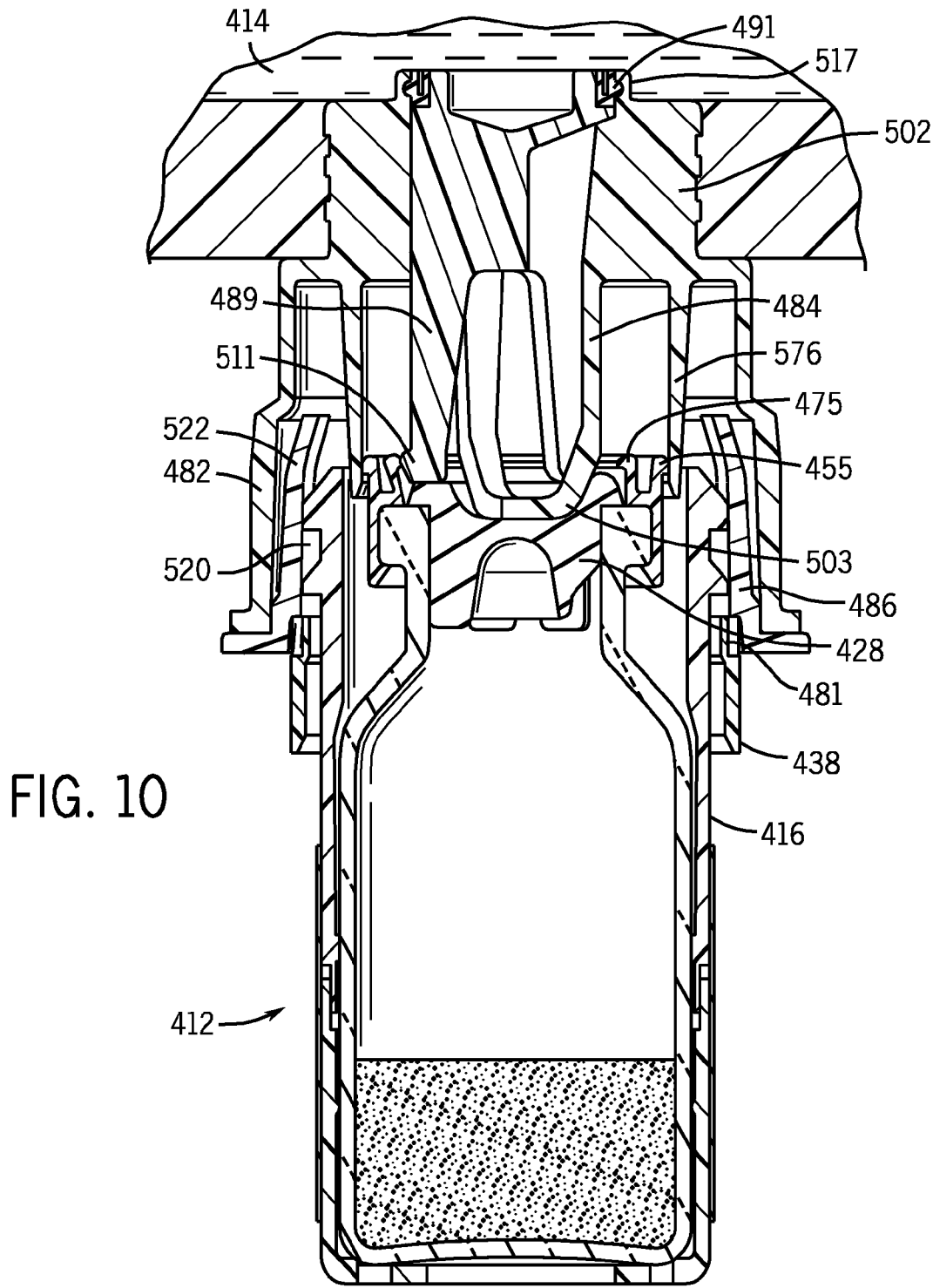
FIG. 10 is a cross-sectional view about the centerline of the first container and second container following docking of the first container (i.e., in the docked position)
Figure 11:
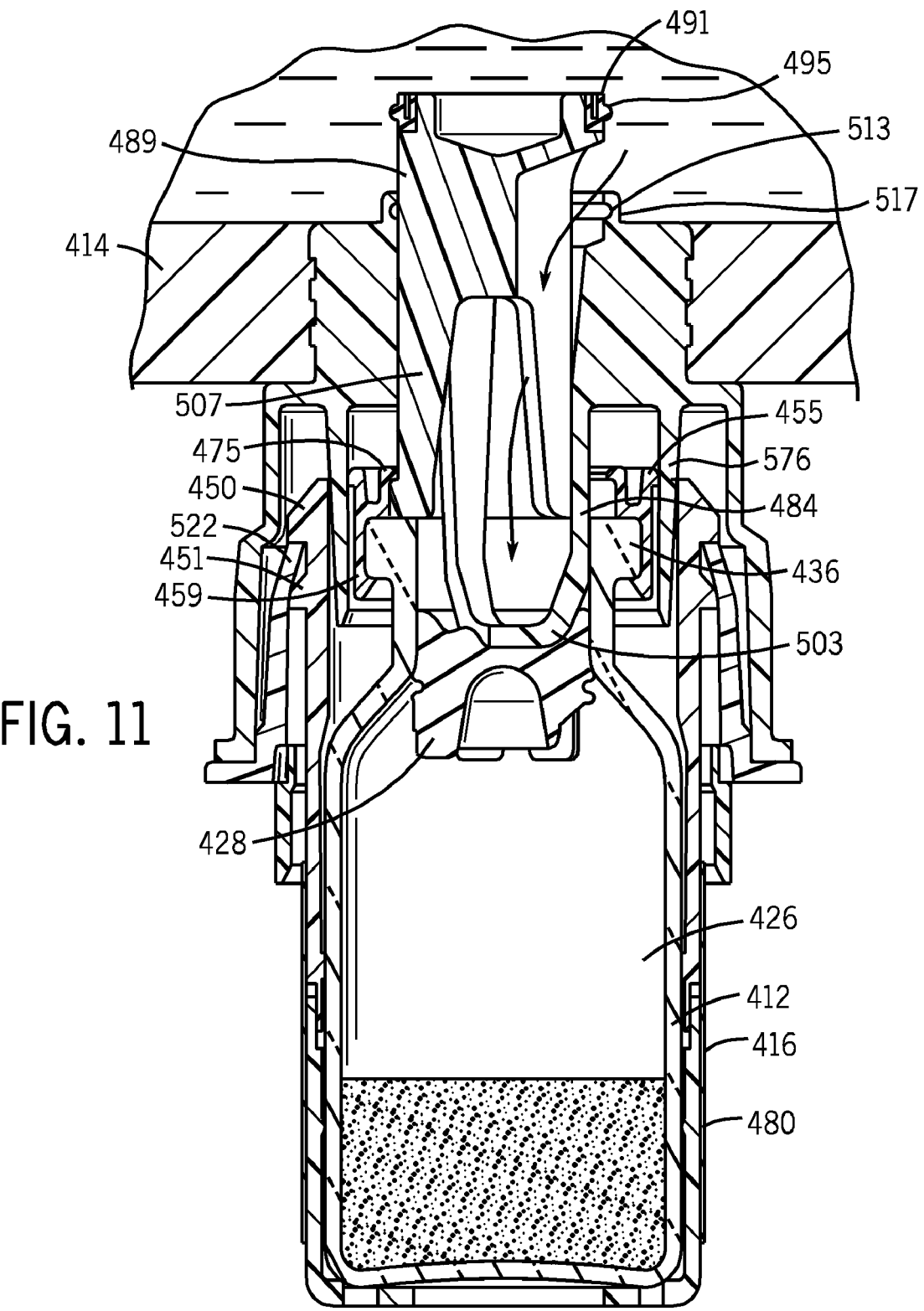
FIG. 11 is a cross-sectional view about the centerline of the first container and second container during activation of the first container.
Figure 12:
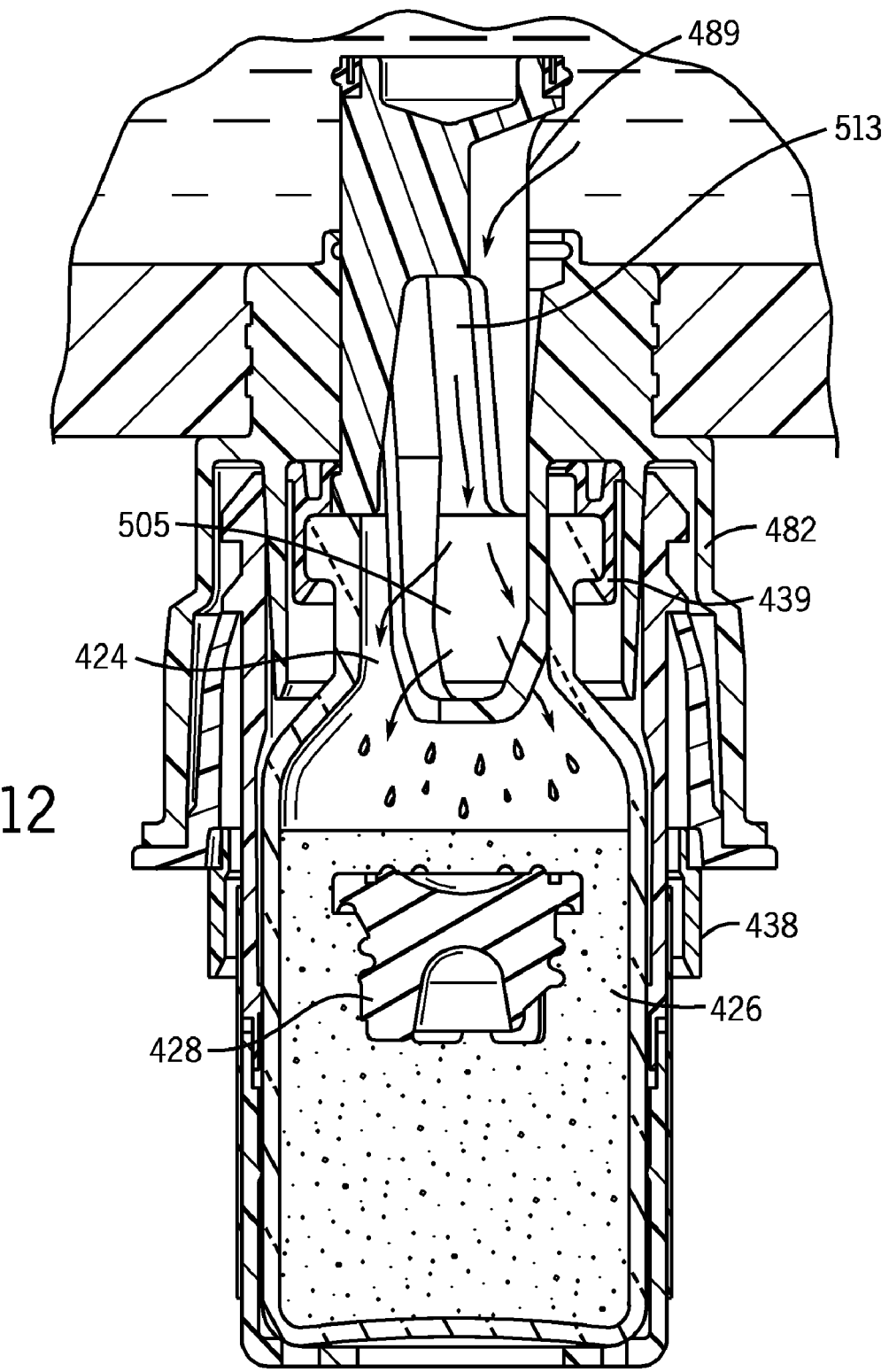
FIG. 12 is a cross-sectional view about the centerline of the first container and second container following activation of the first container; and, FIG. 13 is a perspective view of a method of utilizing a syringe in connection with the medicament in the first container.

The first container 412 has an upper body member 416 or body cap 416 that is adapted to mate with a retainer 486 in the port assembly 418 of the second container 414, as depicted in FIG. 3. The combination of body cap 416 and retainer 486 of the port assembly 418 assist in docking the first container 412 to the second container 414, and also assist in establishing a fluid connection between the interiors of first container 412 and second container 414 in order to enable mixing of the contents of the two containers 412, 414. Typically, to mix or reconstitute the drug in the first container 412, the first container 412 is docked or connected to the port assembly 418 of the second container 414 as shown in FIG. 10, and then the cavities of each container 412, 414 are placed in fluid communication via an activation process, as shown in FIGS. 1 and 11-12, in order to mix the contents of first and second containers 412, 414.

Figure 8:
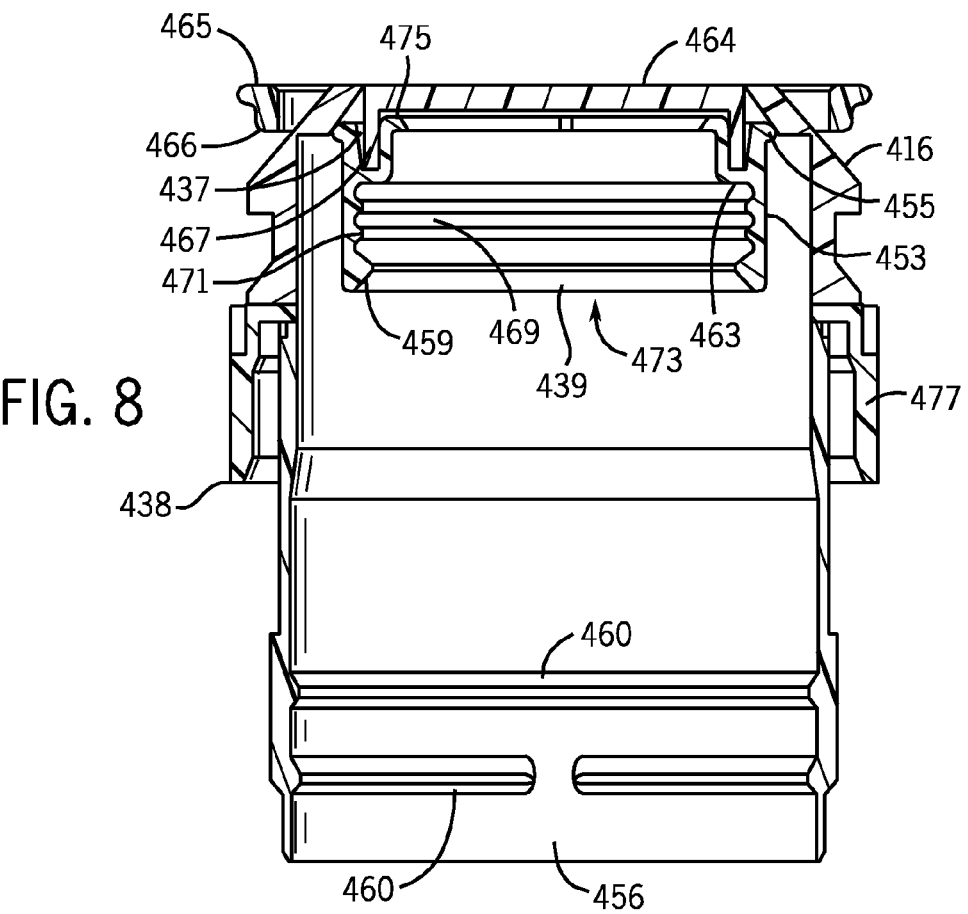
FIG. 8 is a cross-sectional view of the upper housing assembly of the first container about the center-line thereof.

As shown in FIG. 4, in one embodiment the first container 412 is a vial containing a medicament or drug. The medicament or drug can be in any number of different forms, including liquid, gel, or powder (e.g., lyophilized) forms, or in a combination of any of these known forms. The medicament or drug is depicted in FIG. 4 as being a powdered or lyophilized drug. In this embodiment the first container 412 is partially surrounded by a body cap 416, a hanger cap 476 and a label 480. Connected to the body cap 416 is a removable top cap 464 and an activation collar 438. Additionally, as shown in FIG. 8, a seal ring 439 is provided. The seal ring 439 connects around the neck area 422 of first container 412, and is adjacent the interior surface of removable top cap 464 prior to removal of the top cap 464 from the body cap 416. The seal ring 439 prevents any of the diluent and/or medicament from escaping out of the fluid flow path between the first container 412 and the second container 414.

First container 412 can be in the form of a vial can be constructed from a variety of known materials, including glasses, plastics, and any other commercially acceptable materials. The first container 412 generally has a body portion 420 and a neck 422 extending therefrom. The neck 422 of the first container 412 surrounds an opening 424 leading to an internal cavity 426 that houses the contents, such as a medicament or drug, in the first container 412. In one embodiment the neck 422 of the first container 412 also has an outwardly extending annular portion 436 adjacent the opening 424 of the first container 412.

A stopper 428 is provided in the opening 424 of the first container 412. Stopper 428 is operable to seal first container 412. The stopper 428 closes the opening 424 and prevents the contents in the internal cavity 426 from escaping out of the cavity 426 of the first container 412. The stopper 428 also prevents external components from unintentionally entering the cavity 426 of the first container 412. The stopper 428 has a body portion 430 that is configured to be positioned within the neck 422 of the first container 412, and a top surface 432 that is outwardly facing from the neck 422 of the first container 412 when the stopper 428 is in the position shown in FIG. 9. In one embodiment the top surface 432 of the stopper 428 has a depression 433 to assist in reducing the forces necessary to transition the stopper 428 to a second position within the first container 412. In an alternate embodiment, there is no depression 433 in the top surface 432 of the stopper 428. Additionally, in a preferred embodiment the stopper 428 also has a flange 434 extending from the body portion 430. The flange 434 is beneficial for maintaining the stopper 428 placement in the first container 412 when a syringe or cannula is inserted through stopper 428 to make solution additions and/or to withdraw material from the first container 412, and for providing an air and/or moisture seal when the first container 412 is connected to the port assembly 418 of the second container 414. In the embodiment depicted in FIG. 9, an undercut 429 is provided about the circumference of stopper 428 at the point at which the underside of flange 434 meets the stopper body portion 430. Undercut 429 serves as a hinge or folding point to assist in reducing the stopper push-in force, i.e., the force required to push stopper 428 into the interior of first container 412 when the system of the present invention is moved to the activated position. Undercut 429 enables flange 434 to hinge or fold upwardly during activation of the system. For example, in the position shown in FIG. 9, the flange 434 of the stopper 428 rests on the top of the outwardly extending annular portion 436 of the neck 422 of the first container 412, i.e., flange 434 has been folded upwardly due to the application of an inwardly directed activation force. In the depicted embodiments of stopper 428, undercut 429 is in the form of a groove having a width in the range of 0.03 inches to 0.1 inches. In an alternative embodiment, the width of undercut 429 is in the range of 0.04-0.07 inches. It will be appreciated by those of ordinary skill in the art that the dimension and shape of undercut 429 will vary depending upon (a) the material from which stopper 428 is constructed; and (b) the target force required to push stopper 428 into the interior of first container 412 when the system of the present invention is activated, as described in detail herein.

Figure 9:
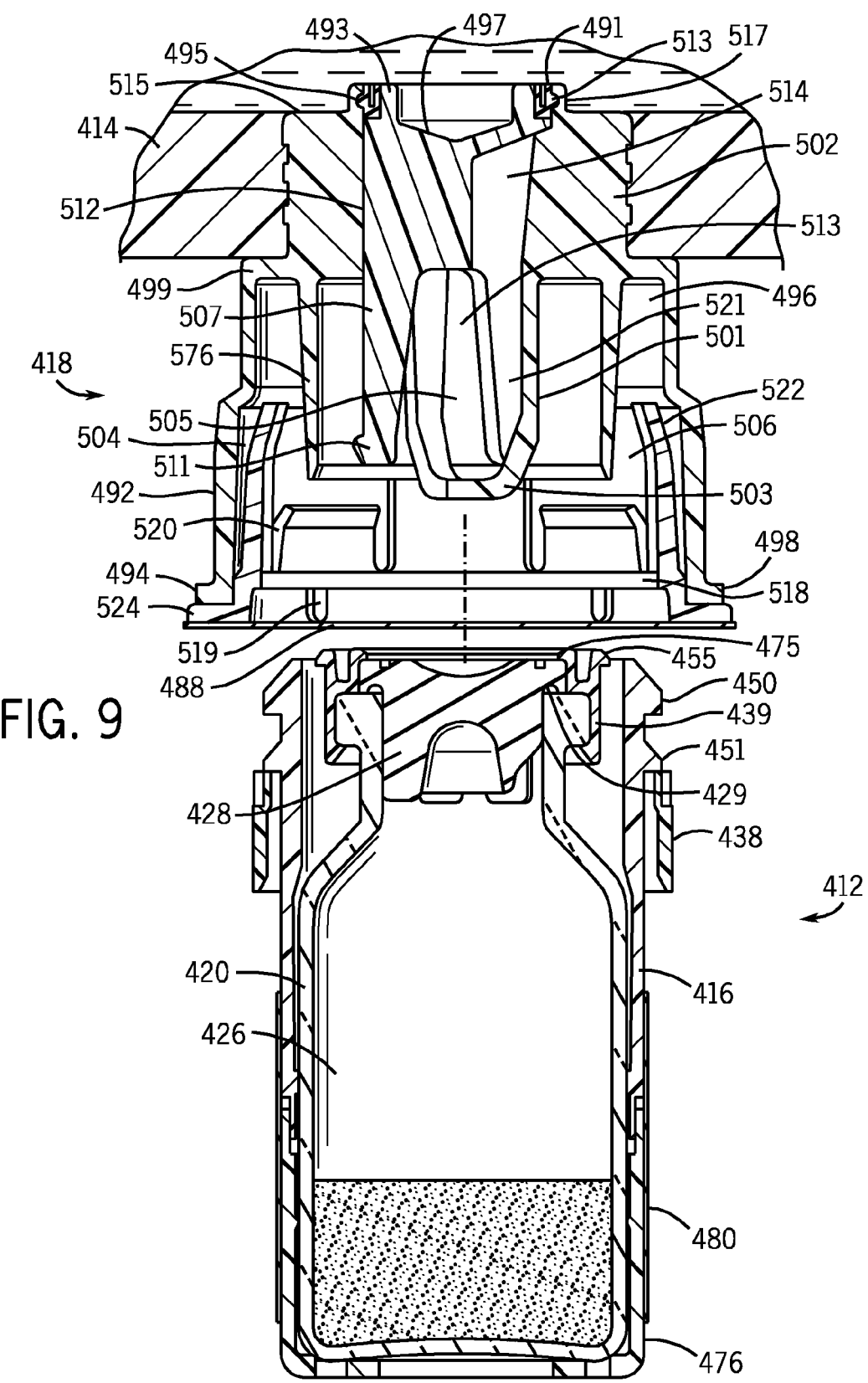
FIG. 9 is a cross-sectional view about the centerline of the first container and second container prior to docking of the first container.

Referring to the exploded view and the cross-sectional view of the first container 412 as shown in FIGS. 4 and 9, in one embodiment the body cap 416 is generally positioned around the neck portion 422 and the body portion 420 of the first container 412. More specifically, the body cap 416 has an internal cavity 456 that houses at least a portion of the body 420 of the first container 412. The body cap 416 thus generally covers the upper portion of the first container 412 and assists in docking the first container 412 to the second container 414, as well as assisting in activating the system 410.

As shown in FIGS. 4 and 9, the body cap 416 has a sidewall 442. A track 441 is provided in the sidewall 442 of the body cap 416. As explained herein, the track 441 guides the movement of the first container 412 in combination with the activation collar 438 during the transition of the first container 412 from the docked position to the activated position. In the embodiment depicted in FIG. 4, track 441 is an indent or recess in the sidewall 442 of the body cap 416. The track 441 is designed to receive a protrusion 479 extending from the activation collar 438 such that protrusion 479 can move therein. The track 441 has a first vertical portion 443, a horizontal portion 445, and a second vertical portion 447. The track 441 also has at least one defeatable stop 449. In one embodiment a defeatable stop 449 is provided in the first vertical portion 443. In an alternative embodiment, another defeatable stop 449 is provided in the horizontal portion 445 of the track 441. The defeatable stop 449 operates to preclude movement of the activation collar 438 by not allowing the protrusion 479 on the inner sidewall of the activation collar 438 to pass over the defeatable stop 449 until a certain amount of force is applied, whereupon the stop is "defeated" and further movement becomes possible. The first vertical portion 443 of the track 441 is relatively short, and is generally provided to allow for a small amount of movement in overcoming the defeatable stop 449. Conversely, the second vertical portion 447 of the track 441 is longer to allow for complete axial movement of the first container 412 with respect to the second container 414 which results in activation of the system 410, as explained in detail below. The second vertical portion 447 of the track 441 has an activation marker 485 which cooperates with the activation marker 483 to provide a visual indication of proper rotational alignment of the first container 412 for activation. The horizontal portion 445 of the track 441 joins the first vertical portion 443 and the second vertical portion 447 to provide a single continuous track. The horizontal portion 445 allows for rotational movement of the body cap 416 with respect to the activation collar 438 (which is maintained stationary via its splines 481 as identified herein) such that the activation marker 485 on the body cap 416 will align with activation marker 483 on the activation collar 438 (see FIGS. 4-7). In an alternative embodiment, the body cap 416 has first and second tracks 441 spaced 180° apart on the sidewall 442 of the body cap 416, and the activation collar 438 has mating first and second protrusions 479 spaced 180° apart. In another alternative embodiment, the body cap 416 has first, second, and third tracks 441 spaced 120° apart on the sidewall 442 of the body cap 416 and the activation collar 438 has mating first, second, and third protrusions 479 spaced 120° apart.

The body cap 416 also has a first mating member that engages a second mating member of the port housing assembly 418. In a preferred embodiment the first mating member of the body cap 416, and thus first container 412, comprises first and second annular flanges 450, 451 that extend radially outward from a distal portion of the sidewall 442 of the body cap 416, as shown in FIGS. 4-8. The first annular flange 450 is positioned adjacent the distal end of the body cap 416, and the second annular flange 451 is positioned a predetermined distance below the first annular flange 450. In one embodiment, the first annular flange 450 of the first mating member is utilized to assist in centering the first container 412 in the port housing 482 (see FIGS. 9 and 10) and docking the first container 412 to the port housing 482 in the docked position (see FIG. 10). The second annular flange 451 of the first mating member is utilized to assist in maintaining the first container 412 in the fully activated position (see FIG. 12). In the depicted embodiments of the present invention, the first and second annular flanges 450, 451 have circular circumferential perimeters that are sized and shaped to fit within the opening to the retainer 486 of the port housing 482, and to engage the tabs 520, 522 of the retainer 486 of the port housing 482. In alternative embodiments, first and second annular flanges 450, 451 have interrupted circumferential perimeters, i.e., one or more gaps or voids are present about the circumference.

As explained above, the top cap 464 of the body cap 416 is removable. As shown in FIGS. 4 and 8, the top cap 464 has a pull ring 465 associated therewith. The top cap 464 provides an integral cap for the first container 412 that prevents the first container 412 from being docked to the second container 414 prior to removal of the top cap 464, and it also protects the first container 412 from any attempted tampering by generally providing a protective seal over the opening to the body cap 416 to seal the internal cavity 456 of the body cap 416, including all components and surfaces interior of the body cap 416, from the outside environment and to provide sterility to the area in the interior of the body cap 416. Thus, one cannot access the contents of the first container 412 when the top cap 464 is still connected to the body cap 416. The top cap 464 also has a circumferential rib 467 that protrudes axially downward into the cavity of the body cap 416. As shown in FIG. 8, the circumferential rib 467 engages an annular depression 437 in the top of the seal ring 439 to assist in properly aligning the first container 412 in the body cap 416. In one embodiment, the body cap 416 and top cap 464 are manufactured integrally from a low density polyethylene. It will be appreciated that a variety of materials, and combinations of materials, can be used in the manufacture of body cap 416 and top cap 464. A thin wall 466 joins the top cap 464 to the body cap 416. The thin wall 466 can be ruptured to disconnect the top cap 464 from the body cap 416. To remove the top cap 464, the user pulls on the pull ring 465, which in turn ruptures the thin wall 466 connecting the top cap 464 to the body cap 416, thereby disconnecting the top cap 464 from the remainder of the body cap 416 (see FIG. 9). Because thin wall 466 is ruptured in the process of removing top cap 464 from body cap 416, top cap 464 cannot be reattached, thus providing evidence of possible tampering with the contents of first container 412.

Referring to FIG. 8, the body cap 416 also has first and second rib seals 460. The rib seals 460 are preferably protrusions extending radially inwardly from the interior surface of the body cap 416 into the cavity 456 of the body cap 416 to engage the first container 412 and provide a seal against contaminants entering the cavity 456 of the body cap 416. In one embodiment each rib seal 460 is interrupted at approximately 180° to allow for venting of the cavity 456, however, the interruptions of the first rib seal 460 are offset 90° from the interruptions of the second rib seal 460 to provide an interrupted, tortuous path for the preservation of sterility of the cavity 456 of the body cap 416 and the contents thereof.

Seal ring 439 is configured to engage the neck area 422 of the first container 412. As shown in FIG. 8, the seal ring 439 comprises a generally cylindrical component having a sidewall 453. The sidewall 453 has a first flange 455 extending radially outward from the sidewall 453 at an upper first end portion thereof, and a second flange 459 extending radially inward from the sidewall 453 at a lower second end portion thereof. The seal ring 439 also has an internal shoulder 463. The internal shoulder 463 and the second flange 459 cooperate to create a recess 469 to receive and retain the outwardly extending annular portion 436 of the neck 422 of the first container 412. Additionally, the seal ring 439 has a series of radially inwardly extending annular ribs 471 extending from the sidewall 453 of the seal ring 439 to seal against the neck 422 of the first container 412. As explained above, the seal ring 439 also has an annular depression 437 in the top of the seal ring 439 to receive the annular rib 467 extending from the top cap 464. Finally, the seal ring 439 has a first opening 473 adjacent the second flange 459, through which the vial 412 enters to engage the seal ring 439, and a second opening to provide access to the stopper 428 when the seal ring 439 is connected to the first container 412. The seal ring 439 also has an inner flange 475 extending radially inward and opposing the first flange 455. The inner flange 475 engages the legs 507 of the plug 489 as is explained herein. In one embodiment the seal ring 439 is made of a plastic material, and preferably a thermoplastic polyester elastomer. Thermoplastic polyester elastomeric materials generally provide the flexibility of rubbers, the strength of plastics and the processibility of thermoplastics. They can be processed easily by conventional thermoplastic processes like injection molding, blow molding, calendaring, rotational molding, extrusion and meltcasting.

Referring to FIGS. 4-9, an activation collar 438 is connected to the outer sidewall of the body cap 416. The activation collar 438 in combination with the body cap 416 assist in controlling movement of the first container 412 as the first container 412 is docked to the port assembly 418. The activation collar 438 has a cylindrical sidewall 477 with a protrusion 479 extending inwardly from the inner surface of the sidewall 477, as discussed above. The protrusion 479 is a mating member that mates with the track 441 in the sidewall 442 of the body cap 416. In one embodiment of the present invention, the activation collar 438 has first and second protrusions 479 spaced 180° apart. Similarly, the body cap 416 has first and second tracks 441 spaced 180° apart on the sidewall 442 of the body cap 416. It will be appreciated the number and configuration of protrusions 479 and tracks 441 can be varied without departing from the spirit and scope of the present invention. The engagement between the protrusions 479 on the activation collar 438 and the tracks 441 on the body cap 416 maintain the activation collar 438 connected to the outer sidewall of the body cap 416, and are explained in detail herein. Additionally, the protrusion 479 on the activation collar 438 and the track 441 cooperate as a stop following docking of the first container 412 in the port housing 482 of the second container 414 to preclude unintentional activation of the first container 412.

The activation collar 438 also has a plurality of splines 481 extending from the sidewall 477 thereof. In one embodiment the splines 481 extend from an exterior surface of the sidewall 477 of the activation collar 438. In one embodiment, the activation collar 438 has 36 splines 481. According, in that embodiment the splines 481 are spaced every 10°. However, it will be appreciated that the number of splines 481 can be varied. The splines 481 of the activation collar 438 engage a mating protrusions 519 on the port assembly 418 (see FIG. 9) to preclude rotation of the activation collar 438 when the first container 412 is attached or "docked" to the second container 414. Such engagement is explained in detail herein. In the configuration of the present invention wherein 36 splines 481 are provided, the maximum angular rotation required to have the splines 481 of the activation collar 438 engage the mating protrusions 519 of the port assembly 418 is 5°. Additionally, in a preferred embodiment, the splines 481 on the outer surface of the activation collar 438 have a chamfered lead-in to assist in mating the splines 438 with the mating protrusions 519 as explained herein. The activation collar 438 also has an activation marker 483 to provide a visual indication of proper rotational alignment of the activation collar 438 with the body cap 416 for activation. In a preferred embodiment the activation collar 438 is made of a polypropylene material. As shown in FIG. 10, the outer surface of the body cap 416, including the activation collar 438, has a circumference that is smaller than the opening to the port housing 482. In this manner, the body cap 416 secured to the first container 412 can be inserted into the port housing 482 for docking and subsequent activation of the first container 412.

As shown in FIGS. 1, 4, and 9, the first container 412 has a hanger cap 476 provided at the distal end of the body portion 420 of the first container 412. In one embodiment, the hanger cap 476 has a shape generally consistent with the shape of the distal end of the body portion 420 of first container 412. In the depicted embodiment, the hanger cap 476 has a generally cylindrical shape. The hanger cap 476 also has a hingeable connector 478 extending therefrom. As shown in FIG. 1, the connector 478 can be pivoted from the lower portion of the hanger cap 476 to assist in hanging the reconstitution system 410, such as from conventional IV pole or other structure configured for holding an IV bag.

Referring now to FIGS. 1, 2, 4-7, and 9, in one embodiment the first container 412 has a label 480 that connects the body cap 416 to the hanger cap 476, and secures the body cap 416 and the hanger cap 476 on the first container 412. As shown in FIG. 9, in such an embodiment when the body cap 416 and hanger cap 476 are fully seated on the first container 412, a gap of approximately 0.060" exists between mating ends of the body cap 416 and the hanger cap 476.

The reconstitution system 410 also has an activation marker 487. In one embodiment the activation marker 487 is a colored band 487 on the label 480 joining the body cap 416 to the hanger cap 476. As explained herein, the activation marker 487 is visible when the first container 412 is docked to the second container 414 (see FIG. 5), as well as during the process of activation (see FIG. 6), however, after full activation has occurred the activation marker 487 becomes hidden under the activation collar 438 (see FIGS. 1 and 7). Accordingly, a positive visual indication that full and complete activation has occurred is provided when the activation marker 487 is no longer visible.

Referring now to FIGS. 1-3, the second container 414 has a port assembly 418 that is adapted to engage the body cap 416 of the first container 412 to dock the first container 412 on the second container 414. Accordingly, one function of the port assembly 418 is as a receiver for docking the drug vial 412. The port assembly 418 also includes a structure to facilitate fluid communication between the first container 412 and the second container 414 for activation, admixing, and/or reconstitution of the medicament in the first container 412.

As shown in FIG. 3, the port assembly 418 generally comprises a port housing 482, an actuator 484, a plug 489, a retainer 486, a peelable cover 488 and an overcap 490. In the embodiment of the present invention depicted in FIG. 3, the retainer 486 of the port assembly 418 is a retainer or docking member 486. Portions of the retainer 486 engage the first mating member (i.e., the first and second flanges 450, 451) of the first container 412 during docking and activation of the first container 412. The peelable cover 488 and overcap 490 assist in maintaining the sterility of the contents of the port assembly 418. Peelable cover 488 and overcap 490 also provide evidence of tampering with the contents of second container 414.

As best shown in FIGS. 3 and 9, the port housing 482 of the port assembly 418 has a first housing portion 492 having a first end 494 and a second end 496. A flange 498 extends radially outwardly from the first end 494 of the first housing portion 492, and a shoulder 499 extends radially inwardly from the second end 496 of the first housing portion 492. Another housing portion 502 extends from the first housing portion 492. In one embodiment, as shown in FIGS. 1 and 9, wherein the second container 414 is a flexible diluent bag, the second container 414 is fixedly connected to the outer wall of housing portion 502 of the port housing assembly 418 to connect the port assembly 418 with the interior cavity 415 of the second container 414. In such an embodiment housing portion 502 preferably has a semi-elliptical outer shape (as depicted in FIG. 3) to assist in sealing the second container 414 to the port housing 482.

The first housing portion 492 of the port housing 482 has an interior surface 504 defining a first cavity 506, and housing portion 502 has an interior wall 512 defining another cavity or interior bore 514 of the port housing 482. The port housing 482 has an annular recess 513 provided adjacent the exit to the bore 514 at the distal end 515 of housing portion 502. In the embodiment depicted in FIG. 9, a raised lip 517 is provided.

The plug 489 of the port assembly 418 is positioned in the bore 514 of the port housing 482. The plug 489 has a seal member 491 positioned within or at the end of housing portion 502 to prevent fluid from escaping into or out of the second container 414 through the inner bore 514 of port housing 482. The plug 489 fluidly separates the interior cavity 415 of the second container 414 from the interior bore 514 of the port housing 482.

The port housing 482 also has an interior seal wall 576 extending axially into the first cavity 506 of the first housing portion 492 from the shoulder 499 at the second end portion 496 of the first housing portion 492. In one embodiment the interior seal wall 576 is generally cylindrically shaped, and is concentrically positioned with respect to the interior surface 504 of the first housing portion 492 of the port housing 482. In a second embodiment, the interior seal wall 576 is slightly tapered. The interior seal wall 576 extends downwardly and contacts or engages the first flange 455 extending radially outwardly from the sidewall 453 at an upper first end 457 of the seal ring 439 during activation of the first container 412. The engagement of the interior seal wall 576 with the first flange 455 of the seal ring 439 during activation of the first container 412 operates as a seal. As explained herein, when the first container 412 is transitioned axially toward the second container 414 during the activation step, the first flange 455 of the seal ring 439 will slide on the interior seal wall 576, as shown in FIGS. 10-12. A seal is created between the interior seal wall 576 and the first flange 455 of the seal ring 439.

As explained above, the port assembly 418 has an actuator 484. In one embodiment, the actuator 484 is integral with the port housing 482. As shown in FIGS. 3 and 9, the actuator 484 extends axially into the first cavity 506 of the first housing portion 492 from the shoulder 499 at the second end 496 of the first housing portion 492. The actuator 484 is further positioned radially inwardly and generally concentrically to the interior seal wall 576 of the port housing 482. The actuator 484 is formed of a plurality of ribs or sidewall members 501 that extend from the shoulder 499 of the port housing 482 and terminate at a bottom 503. In a preferred embodiment, the actuator 484 is comprised of three sidewall members or ribs 501 with axial gaps 505 between each sidewall member or rib 501. The sidewall members or ribs 501 define a central cavity 521 of the actuator 484, and the axial gaps 505 provide access to the central cavity 521. The central cavity 521 ultimately becomes a fluid flow path. The outside diameter of the sidewall members or ribs 501 approximates the inside diameter of the opening 424 of the first container 412. The distal end of the sidewall members or ribs 501 can be tapered inwardly toward actuator bottom 503. As is explained herein, the actuator 484 is preferably constructed of a relatively rigid material, e.g., a rigid plastic, so that it can be used to displace the stopper 428 into the internal cavity 426 of the first container 412 as shown in FIGS. 11-12. The large axial gaps 505 of the actuator 484 facilitate fluid communication with the contents of the first container 412 when the actuator 484 is positioned within the opening 424 of the first container 412. In a preferred embodiment the port housing 482 and its integral actuator 484 are made of a polypropylene copolymer.

As explained above, the plug 489 of the port assembly 418 is positioned within the bore 514 defined by the interior wall 512 of housing portion 502. The plug 489 has an end wall 497 with an annular seal member 491 at the distal end 493 thereof. The seal member 491 surrounds the circumference of the distal end 493 of the plug 489. An annular rib 495 of the seal member 491 engages the annular recess 513 in the port housing 482 to seal the interior cavity 415 of the second container 414 from the interior bore 514 of the port housing 482. The plug 489 also has a plurality of legs 507 extending axially away from a main body 509 of the plug 489. In a preferred embodiment, the plug 489 has three legs 507 as shown in FIGS. 3 and 9. A radial extension 511 is provided at the terminal end of each leg 507. As is explained herein, the radial extensions 511 of the legs 507 are provided to engage the seal ring 439. Finally, a cavity 513 is defined between the legs 507 of the plug 489. The cavity 513 is fully accessible through the gaps between the legs 507 of the plug 489 and at the distal open end of the plug 489.

As best shown in FIGS. 3 and 9, the retainer or docking member 486 is located within the first cavity 506 of the first housing portion 492 of the port housing 482. The retainer 486 comprises a body portion having a base 518, a plurality of different length tabs 520, 522 extending from the base 518, and a flange 524 extending from a proximal end of the retainer 486. The retainer 486 also has one or more protrusions 519 extending from an interior surface of the base 518. The protrusions 519 mate with the space between the splines 481 on the outer surface of the activation collar 438. In one embodiment, the protrusions 519 in combination with the geometry of the base 518 also operate as a stop for the activation collar 438 when the first container 412 is inserted into the port assembly 418 (shown in FIG. 10) for docking of the first container 412 therein. In one embodiment the flange 524 of the retainer 486 is fixed to the flange 498 of the port housing 482, e.g., the upper surface of the flange 524 of the retainer 486 is ultrasonically welded to the lower surface of the flange 498 of the port housing 482. Accordingly, in such an embodiment the retainer 486 is fixed in the port housing 482. Retainer 486 and port housing 482 can be formed from a single piece of material or from multiple components without departing from the scope of the present invention.

As shown in FIGS. 3 and 9-12, and explained above, the retainer 486 has a plurality of tabs 520, 522. In one embodiment, a first set of tabs 520 are shorter in height than a second set of tabs 522. In this embodiment, the first set of tabs 520 is utilized to support the first container 412 in the docked position as shown in FIG. 10, and the second set of tabs 522 is utilized to support the first container 412 in the activated position as shown in FIG. 12. Each of the tabs 520 and 522 can include a tapered portion at the distal end thereof. Retainer 486 can be constructed of a flexible material, such as plastic, e.g., a polypropylene copolymer, to allow the tabs 520, 522 to be flexed when the first container 412 is inserted into the port housing 482, and thereafter allowing tabs 520, 522 to spring back into their original position. Accordingly, tabs 520 and 522 allow the first container 412 to be pushed in a first axial direction toward the second container 414, but resist movement backward in the opposing direction to prevent the first container 412 from being removed from engagement with the port housing 482 following docking and activation of the first container 412.

Referring to FIGS. 9-12, as the first container 412 is inserted into the port housing 482, the first annular flange 450 centers the first container 412 in the opening at the proximal end the retainer 486 of the port housing 482. As the first container 412 is pushed axially inward, the first annular flange 450 flexes the distal end of the first set of tabs 520 radially outwardly to allow the first annular flange 450 to extend axially inwardly of the tabs 520. When the first annular flange 450 is positioned inwardly of the first set of tabs 520, the tabs 520 will flex back and return to their original, unflexed positions. In this position, as shown in FIG. 10, the annular flange 450 is docked on the first set of tabs 520, and the first set of tabs 520 prevent the annular flange 450, and thus the first container 412, from being pulled out of the retainer 486. In this way the system prevents first container 412 from being "undocked" from second container 414 after the docking process has been completed, thereby minimizing the possibility of tampering and/or the compromising of the sterility of the system. Further, in this position the splines 481 on the activation collar 438 engage the protrusions 519 on the retainer 486 to prevent the activation collar 438, and moreover, the entire first container 412, from rotating within the port housing 482.

After the first container 412 is docked in the port housing 482, the system 410 can be activated at any subsequent time. To activate, the first container 412 is initially moved axially inwardly toward the port housing 282, such that the protrusion 479 on the activation collar 438 overcomes the defeatable stop 449 (see FIG. 5). Next, the first container 412 is rotated with respect to the fixed activation collar 438, by rotating the first container 412 (see FIG. 6). As explained above, movement of the first container 412 is limited to that allowed by the track 441. After the first container 412 is rotated such that it has exhausted the possible translation of the protrusion 479 in the horizontal portion 445 of the track 441, the first container 412 can again be axially translated toward the second container 414 and further within the port housing 482 (see FIG. 7).

While the activation step has been identified functionally above, it will herein be described structurally. As the first container 412 is pushed axially inwardly on the second vertical track portion 447 and into the first cavity 506 of the port housing 482, the first annular flange 450 will contact the distal end of the second set of tabs 522 and flex the second set of tabs 522 radially outwardly to allow the first annular flange 450 to extend axially inwardly of the second set of tabs 522 (see FIG. 11). This is referred to as the partially activated position. To obtain full activation, as shown in FIG. 12, the first container 412 must be pushed even further axially inwardly on the second vertical track portion 447 and into the first cavity 506 of the port housing 482. As shown in FIG. 12, the second annular flange 451 will contact the distal end of the second set of tabs 522 and flex the second set of tabs 522 radially outwardly to allow the second annular flange 451 to be positioned axially inwardly of the second set of tabs 522. When the second annular flange 451 is positioned inwardly of the second set of tabs 522, the tabs 522 will flex back and return to an unflexed position (see FIG. 12). This is referred to as the activated or fully-activated position. In this position, the second annular flange 451 is positioned on the second set of tabs 522, and the second set of tabs 522 prevents the second annular flange 451, and thus the first container 412, from being pulled out of the retainer 482. In this position the first container 412 is prevented from further axial movement toward the second container 414. These features prevent intentional tampering as well as other activities that could compromise the sterility of the contents of first container 412 and second container 414.

In the embodiment of the present invention shown in FIG. 3, the port assembly 418 also includes a peelable cover 488. The peelable cover 488 is positioned on the flange 424 of the retainer 486 connected to the port housing 482 to provide a protective seal over the opening to the port assembly 418 and to seal the interior of the port assembly 418, including all components and surfaces thereof, from the outside environment and to provide sterility to this area. In one embodiment the peelable cover 488 is made of Tyvek® material (or other known materials) and an appropriate adhesive on one side thereof to facilitate the bonding of peelable cover 488 to retainer 486. Peelable cover 488 can have one or more tabs or extensions to assist in its removal from retainer 486. An overcap 490, preferably made of a plastic material, is preferably constructed to serve as a protector for the peelable cover 488. In the embodiment depicted in the attached figures, the overcap 490 has a pair of sidewalls and flanges that grasp around the peelable cover 488 and onto the flange 498 of the port housing 482 to retain the over cap 490 on the port assembly 418.

In one embodiment of the present invention, in order to mix or reconstitute the contents of the first container 412 with the contents of the second container 414, the first container 412 is docked or connected to the port assembly 418 of the second container 414 as shown in FIG. 1. As explained herein, following the docking step, the cavities of each container 412, 414 are placed in fluid contact through an activation process, whereby the contents of the first and second containers 412, 414 can be combined or admixed.

Referring to FIG. 2, the first container 412 can be maintained separate from the second container 414 until the drug is requested by a doctor. After a prescription is ordered, a pharmacist or clinician will remove the top cap 464 from the body cap 416 of the first container 412. The pharmacist or clinician also will remove the over cap 490 and peelable cover 488 from the port housing assembly 418. The first container or drug vial 412 is now available to be "docked" onto the port assembly 418, typically in the pharmacy, by pushing the drug vial 412 into the port assembly 418, as shown in FIGS. 10-12. When the first container 412 is moved axially into the port assembly 418, the first annular flange 450 contacts the first set of short tabs 520 and flexes the short tabs 520 radially outwardly to allow the first flange 550 to move past the tabs 520. After the flange 450 passes the end of the tabs 520, the tabs 520 will spring back to their original, unflexed positions, thereby locking first container 412 in the docked position relative to second container 414. As the flange 450 is forced past the first set of tabs 520 the pharmacist will typically hear an audible "pop," signaling that the flange 450 has passed over the tabs 520 and that the vial 412 is docked and locked in the ready position. Further, in this position, the tabs 520 preclude reverse axial movement and thus do not allow the first container 412 to be removed from the port housing 482. In addition to preventing possible tampering, the locking of first container 412 in the docked position ensures that first container 412 is not inadvertently disconnected from second container 414 prior to activation. Such disconnection could occur during transport of the first container 412 and second container 414 (by known means such has by hand, by medicine cart, or by pneumatic system) or during storage of the docked system.

Additionally, during docking the first flange 455 that extends radially outward from the sidewall 453 of the seal ring 439 engages the tapered interior seal wall 576. Due to the engagement of the flange 455 on the tapered interior seal wall 576, a seal is created between the interior seal wall 576 and the first flange 455 of the seal ring 439. As shown in FIG. 10, during docking, the bottom 503 of the actuator 484 engages the top surface 432 of the stopper 428 and exerts a minor force on the stopper 428.

In the docked state, as shown in FIG. 10, the contents of the first container or drug vial 412 remain separate from the contents of the second container or diluent bag 414, however, the first container 412 is fixed to the port assembly 418 and second container 414, and cannot be removed therefrom without generally destroying various of its components. Thus, at this point the drug vial 412 is mechanically connected to the port assembly 418, but is not fluidly connected to the diluent bag 414. It is understood that in the docked state the contents of the two containers 412, 414 remain completely separated, and thus the two containers 412, 414 can remain in the docked state without admixing for an extended period typically limited only by the shelf life of the contents in the two containers 412, 414. In the docked state the stopper is positioned in the opening of the vial, thereby providing a moisture and air barrier for the contents of the first container 412. At any time after the drug vial 412 is "docked" on the port assembly 418, a nurse or other clinician can activate the system, thereby enabling mixing or reconstitution of the drug in the first container 412 with the diluent in the second container 414.

Figure 6:
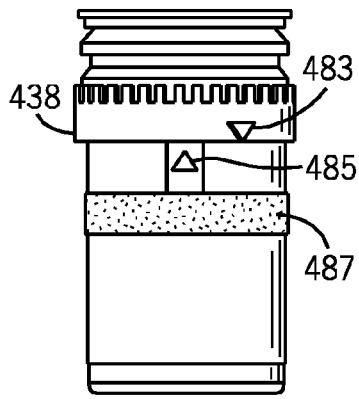
FIG. 6 is a front elevation view of the first container shown in a rotated position prior to final activation.
Figure 7:
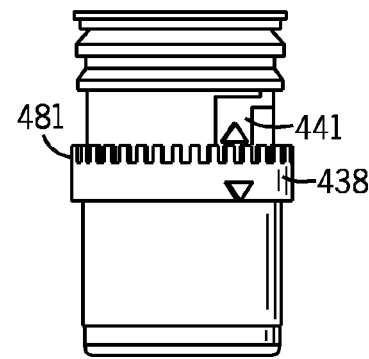
FIG. 7 is a front elevation view of the first container shown in an activated position following simulated activation.

To activate the two-part admixing system 410 the clinician will push the first container 412 axially toward the second container 414. In this step the clinician will have to overcome the defeatable stop 449 by pushing the stop 449 past the protrusion 479 on the inner surface of the activation collar 438 (see FIG. 5). Next, as shown in FIG. 6, the clinician will have to rotate the first container 412 with respect to the fixed activation collar 438 and port housing 482. Again, to preclude unintentional activation, in one embodiment the clinician will have to exert enough of a force to push the stop 449 in the horizontal track portion 445 past the protrusion 479 on the activation collar 438. Finally, as shown in FIGS. 7 and 11-12, the clinician will further push the first container 412 axially toward the second container 414 and into the fully activated position on the second set of tabs 522.

In the final axial activation stage, the seal between the seal member 491 of the plug 489 and the port housing 482 is broken as the plug 489 is forced partially into the cavity of the second container 414. Additionally, the stopper 428 is forced down the opening 424 in the vial 412 and into the inner cavity 426 of the vial 412 as is shown in FIGS. 11 and 12 by the proximal end 503 of the actuator 484, thereby creating a fluid flow path between the first container 412 and the second container 414.

The opening of the fluid flow path to the second container 414 is depicted in FIG. 11. When the first container 412 is pushed axially toward the second container 414 during activation, the legs 507 push past the inner flange 475 of the seal ring 439 and engage the outwardly extending annular portion 436 of the first container 412. Further, the inner flange 475 captures the legs 507 between the inner flange 475 and the lip 436 of the vial 412, maintaining the legs 507 therebetween. Accordingly, as the first container 412 is pushed further axially toward the second container 414 the force will disengage the annular rib 495 of the seal member 491 on the plug 489 from the annular recess 513 in the port housing 482, and force the plug 489 into the cavity of the second container 414, thereby opening the fluid flow path to the second container 414. As shown in FIG. 11, and as explained above, the first flange 455 engages the interior seal wall 576 during activation of the first container 412. The engagement of the interior seal wall 576 with the first flange 455 of the seal ring 439 operates to seal the contents of the second container 414 from escaping out of the port housing 482 and past the first container 412.

As shown in the transition from FIG. 11 to FIG. 12, further axial movement of the first container 412 toward the second container 414 operates to transition the stopper 428 into the cavity 426 of the first container 412, thereby creating a fluid flow between the first container 412 and the central cavity 521 of the actuator 484. In one embodiment, the stopper 428 will ultimately be translated entirely through the opening 424 in the first container 412 and will be deposited within the cavity 426 of the first container 412. At this point the cavity 426 of the first container 412 is open to the central cavity 521 of the actuator 484. As shown in FIG. 12, the central cavity 521 of the actuator 484 has nearly as large a cross section as the opening 424 to the first container 412. This assists the reconstitution system 410 by not restricting the flow of fluid into and out of the first container 412.

As the first container 412 is moved to the fully activated position, the second annular flange 451 of the body cap 416 moves axially up the retainer 486 toward the second container 414 and past the second set of tabs 522. In this position, as shown in FIG. 12, the second annular flange 451 is positioned on the second set of tabs 522, and the second set of tabs 522 prevents the second annular flange 451, and thus the first container 412, from reverse or proximal axial movement (i.e., they prevent the first container 412 from being pulled out of or detached from the port housing 482). This is referred to as the activated position.

An additional aspect of one embodiment of the two-part admixing system 410 is that a visual indication of activation of the system 410 is provided. As shown in FIGS. 1, 2 and 5-7, in one embodiment an activation marker 487 is provided. The activation marker 487 may be a colored or printed band 487 on the label 480 joining the body cap 416 to the hanger cap 476. When the first container 412 is in the docked position the activation marker 487 is visible. This indicates to the clinician that the system 410 has not yet been activated. The activation marker 487 is visible when the first container 412 is docked to the second container 414 (see FIG. 5), as well as during the process of activation (see FIG. 6). After full activation has occurred, the activation marker 487 becomes hidden under the activation collar 438 (see FIGS. 1 and 7). The inability to see the activation marker 487 indicates to the clinician that the admixing system 410 has been activated and that fluid flow between the contents of the two containers 412, 414 is open. The inability of the clinician to see the activation marker 487 also indicates to the clinician that the contents of containers 412, 414 are ready for delivery to a patient, i.e., that the contents of containers 412, 414 have been admixed or diluted for delivery to the patient.

An additional aspect of one embodiment of the two-part admixing system 410, shown in FIG. 13, is that after the top cap 464 is removed from the body cap 416, the contents of the first container 412 can be accessed with a syringe to either remove some of the contents thereof, add a small amount of diluent to the contents thereof, or a combination of adding contents and removing mixed contents from the first container 412. To perform such operations, the clinician may pierce the stopper 428 with the needle of a syringe to access the cavity of the first container 412 as shown in FIG. 13. In this embodiment, first container 412 can be used as a standard pharmaceutical vial, i.e., a vial that is accessed using a hypodermic needle associated with a syringe, and as a component of the two-part admixing system 410 of the present invention. Stopper 428 is preferably constructed of a polymeric material that is resistant to coring when a hypodermic syringe needle is pushed therethrough. The configuration and material of stopper 428 are preferably selected such that the force required to push a hypodermic syringe needle there through is ergonomically acceptable to clinicians. In one embodiment of the present invention, the force required to pierce stopper 428 with a hypodermic syringe needle is less than 1.5 pounds of force. In an alternative embodiment, the force required to force a hypodermic syringe needle through stopper 428 is in the range of 0.5-1.0 pounds of force. The configuration and material of stopper 428 also are preferably selected such that the force required to push stopper 428 into the interior of first container 412 upon activation of the system of the present invention is appropriate in view of the mechanical strength of the system and ergonomics. It will be appreciated that the force required to push stopper 428 into the interior of first container 412 should be great enough to prevent inadvertent activation while simultaneously being small enough to permit both (i) the system of the present invention to be constructed of relatively low-cost materials; and (ii) a clinician to readily move the system into its activated state. In one embodiment of the present invention, the force required to push stopper 428 into the interior of first container 412 is in the range of 4-20 pounds of force. In a second embodiment, the force required to push stopper 428 into the interior of first container 412 is in the range of 5-15 pounds of force. In a third embodiment, the force required to push stopper 428 into the interior of first container 412 is in the range of 8-13 pounds of force. The material used to construct stopper 428 is preferably a material that is inert to the intended contents of first container 412. Where first container 412 is intended to contain a pharmaceutical product, the material of construction of stopper 428 is ideally a material that is already approved by regulatory agencies for use with the pharmaceutical product, thereby minimizing or eliminating the need to undertake extensive compatibility testing to ensure that there is no undesirable interaction between the pharmaceutical product and the stopper 428.

In one embodiment, second container 414 is constructed of a non-PVC, DEHP-free material providing a vapor barrier capability that is sufficient so as to permit diluent or drug product to be stored therein without the use of an overwrap. For example, second container 414 can be constructed of the materials utilized by Hospira, Inc., in the manufacture of its VISIV® flex container.

Several alternative embodiments and examples have been described and illustrated herein. A person of ordinary skill in the art will further appreciate that any of the embodiments could be provided in any combination with the other embodiments disclosed herein. Additionally, the terms "first," "second," "third," and "fourth" as used herein are intended for illustrative purposes only and do not limit the embodiments in any way. Further, the term "plurality" as used herein indicates any number greater than one, either disjunctively or conjunctively, as necessary, up to an infinite number. Additionally, the term "having" as used herein in both the disclosure and claims, is utilized in an open-ended manner.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying claims.

What is claimed is:

1. A medicament container for containing a medicament to be mixed with a diluent in a second container, the medicament container comprising:

a container body having an opening fluidly connected to a cavity defined by said container body;

a stopper positioned within said opening of said container body, said stopper fluidly sealing said cavity defined by said container body from an external environment of said container body;

a body cap positioned around at least a portion of said container body, said body cap having a mating member adapted to mate with a complementary receiver of a second container to connect said medicament container to a second container for mixing a medicament in said medicament container with a diluent in a second container; and a track defined on a perimeter of an exterior wall of said body cap, said track configured to control movement of said medicament container relative to a second container between a docked position and an activated position in which said medicament container is in fluid communication with a second container, wherein controlled axial movement of said medicament container relative to a second container places said medicament container in the activated position by forcing said stopper out of said opening of said container body and into said cavity defined by said container body.

2. The medicament container of claim 1, wherein the track comprises at least one defeatable stop constructed to prevent relative movement between said medicament container and a second container until a predetermined force is applied to overcome said at least one defeatable stop.

3. The medicament container of claim 1, further comprising a connector constructed to allow said medicament container to be hanged.

4. The medicament container of claim 1, further comprising a removable top cap integrally attached to said body cap, said top cap being constructed to preclude access to the stopper when said top cap is positioned on the body cap.

5. The medicament container of claim 4, further comprising a pull-ring associated with said top cap and said body cap, said pull-ring constructed to be detachable from said body cap whereby said top cap is removed from said body cap when said pull-ring is detached from said body cap, and wherein removal of said top cap from said body cap provides access to said stopper.

6. The medicament container of claim 1, further comprising a seal ring, said seal ring having a sidewall having a flange and having ribs extending radially inwardly therefrom, said ribs constructed to seal against said container body.

7. The medicament container of claim 6, wherein said seal ring further comprises an inner flange extending radially inwardly, said inner flange constructed to engage legs of a plug associated with said second container when said medicament container is attached to a second container.

8. The medicament container of claim 1, wherein said mating member comprises an annular flange radially extending from said body cap.

9. The medicament container of claim 8, wherein said flange comprises an interrupted circumferential perimeter.

10. The medicament container of claim 1, wherein said track comprises at least one vertical portion.

11. The medicament container of claim 1, wherein said track further comprises a horizontal portion.

12. The medicament container of claim 1, further comprising an activation collar connected to a perimeter of said body cap, said activation collar having a protrusion extending therefrom configured to engage said track defined on said perimeter of said body cap, said track and said protrusion configured to control movement of said medicament container relative to a second container between said docked position and said activated position.

13. A medicament container for containing a medicament to be mixed with a diluent in a second container, the medicament container comprising:
    an opening fluidly connected to a cavity defined by said medicament container;
    a stopper positioned within said opening, said stopper fluidly sealing said cavity defined by said medicament container from an external environment of said medicament container;
    a mating member adapted to mate with a complementary receiver of a second container to connect said medicament container to a second container for mixing a medicament in said medicament container with a diluent in a second container; and
    a track defined on a perimeter of said medicament container, said track configured to control movement of said medicament container relative to a second container between a docked position and an activated position in which said medicament container is in fluid communication with a second container, wherein controlled axial movement of said medicament container relative to a second container places said medicament container in the activated position by forcing said stopper out of said opening of said medicament container and into said cavity defined by said medicament container.

14. The medicament container of claim 13, wherein the track comprises at least one defeatable stop constructed to prevent relative movement between said medicament container and a second container until a predetermined force is applied to overcome said at least one defeatable stop.

15. The medicament container of claim 13, wherein said track comprises at least one vertical portion.

16. The medicament container of claim 15, wherein said track further comprises a horizontal portion.

17. The medicament container of claim 13, wherein said mating member comprises an annular flange.

18. The medicament container of claim 17, wherein said flange comprises an interrupted circumferential perimeter.

19. The medicament container of claim 13, further comprising an activation collar connected to said medicament container, said activation collar having a protrusion extending therefrom configured to engage said track defined on said perimeter of said medicament container, said track and said protrusion configured to control movement of said medicament container relative to a second container between said docked position and said activated position.

* * * * *